United States Patent
Monaghan et al.

(10) Patent No.: US 9,539,095 B2
(45) Date of Patent: Jan. 10, 2017

(54) POROUS METAL IMPLANTS WITH BONE CEMENT

(71) Applicant: Zimmer, Inc., Warsaw, IN (US)

(72) Inventors: Matthew E. Monaghan, Fort Wayne, IN (US); Timothy A. Hoeman, Morris Plains, NJ (US)

(73) Assignee: Zimmer, Inc., Warsaw, IN (US)

( * ) Notice: Subject to any disclaimer, the term of this patent is extended or adjusted under 35 U.S.C. 154(b) by 158 days.

(21) Appl. No.: 14/513,345

(22) Filed: Oct. 14, 2014

(65) Prior Publication Data

US 2015/0032222 A1    Jan. 29, 2015

Related U.S. Application Data

(63) Continuation of application No. 13/736,614, filed on Jan. 8, 2013, now abandoned.
(Continued)

(51) Int. Cl.
*A61F 2/28* (2006.01)
*A61F 2/30* (2006.01)
(Continued)

(52) U.S. Cl.
CPC .............. *A61F 2/28* (2013.01); *A61F 2/2846* (2013.01); *A61F 2/30767* (2013.01); *A61L 27/04* (2013.01);
(Continued)

(58) Field of Classification Search
CPC ...... A61L 27/56; A61L 27/04; A61B 17/8802; A61F 2/28; A61F 2/30734; A61F 2/30756; A61F 2/30771; A61F 2002/2835; A61F 2002/30011; A61F 2002/30013; A61F 2002/30093; A61F 2002/30757; A61F 2002/4602
See application file for complete search history.

(56) References Cited

U.S. PATENT DOCUMENTS

| | | | |
|---|---|---|---|
| 5,108,399 A * | 4/1992 | Eitenmuller | A61B 17/8047 606/298 |
| 5,282,861 A | 2/1994 | Kaplan | |

(Continued)

FOREIGN PATENT DOCUMENTS

| WO | WO-2009022911 A2 | 2/2009 |
|---|---|---|
| WO | WO-2013106323 A1 | 7/2013 |

OTHER PUBLICATIONS

"U.S. Appl. No. 13/736,614, Advisory Action mailed Jul. 20, 2015", 3 pgs.
(Continued)

*Primary Examiner* — Thomas J Sweet
*Assistant Examiner* — Christie Bahena
(74) *Attorney, Agent, or Firm* — Schwegman Lundberg & Woessner, P.A.

(57) ABSTRACT

An orthopaedic implant for filling a bone void and a method of using the same. The orthopaedic implant comprises an open porous metal portion and a bone cement portion. At a first surface region, the open porous metal portion facilitates bone and/or soft tissue ingrowth into the pores of the first surface region of the open porous metal. At a second surface region, the open porous metal facilitates reception of the bone cement into the pores of the second surface region of the open porous metal. The open porous metal portion of the orthopaedic implant may also be formed of a plurality of porous metal fragments aggregated together with the cement portion of the orthopaedic implant. Additionally, the orthopaedic implant may be pliable and thereby capable of being molded to the shape of a void in a bone.

12 Claims, 11 Drawing Sheets

Related U.S. Application Data

(60) Provisional application No. 61/584,463, filed on Jan. 9, 2012.

(51) Int. Cl.

| | | |
|---|---|---|
| *A61L 27/56* | (2006.01) | |
| *A61L 27/34* | (2006.01) | |
| *A61L 27/42* | (2006.01) | |
| *A61L 27/44* | (2006.01) | |
| *A61L 27/04* | (2006.01) | |
| *A61F 2/34* | (2006.01) | |

(52) U.S. Cl.
CPC ............. *A61L 27/34* (2013.01); *A61L 27/427* (2013.01); *A61L 27/446* (2013.01); *A61L 27/56* (2013.01); *A61F 2/34* (2013.01); *A61F 2002/2825* (2013.01); *A61F 2002/2832* (2013.01); *A61F 2002/2835* (2013.01); *A61F 2002/2892* (2013.01); *A61L 2430/02* (2013.01)

(56) References Cited

U.S. PATENT DOCUMENTS

| | | | | |
|---|---|---|---|---|
| 5,380,328 A | * | 1/1995 | Morgan | A61B 17/8071 606/70 |
| 5,650,108 A | | 7/1997 | Nies et al. | |
| 5,824,088 A | * | 10/1998 | Kirsch | A61B 17/80 424/423 |
| 6,039,762 A | | 3/2000 | McKay | |
| 6,066,176 A | | 5/2000 | Oshida | |
| 6,077,076 A | * | 6/2000 | Comfort | A61C 8/0009 433/173 |
| 6,409,764 B1 | * | 6/2002 | White | A61C 8/0006 424/424 |
| 6,458,162 B1 | | 10/2002 | Koblish et al. | |
| 6,887,278 B2 | | 5/2005 | Lewallen | |
| 7,458,991 B2 | | 12/2008 | Wang et al. | |
| 7,871,561 B2 | | 1/2011 | Kokubo et al. | |
| 8,292,967 B2 | | 10/2012 | Brown et al. | |
| 2005/0112397 A1 | | 5/2005 | Rolfe et al. | |
| 2007/0129809 A1 | | 6/2007 | Meridew et al. | |
| 2007/0150068 A1 | | 6/2007 | Dong et al. | |
| 2007/0233111 A1 | * | 10/2007 | Orbay | A61B 17/1728 606/286 |
| 2009/0099579 A1 | | 4/2009 | Nentwick et al. | |
| 2010/0004754 A1 | | 1/2010 | Brown et al. | |
| 2010/0114316 A1 | | 5/2010 | Swords | |
| 2010/0121458 A1 | | 5/2010 | Ledger et al. | |
| 2011/0130844 A1 | * | 6/2011 | Ratron | A61F 2/30756 623/23.42 |
| 2011/0153028 A1 | | 6/2011 | Albertorio | |
| 2013/0178947 A1 | | 7/2013 | Monaghan et al. | |

OTHER PUBLICATIONS

"U.S. Appl. No. 13/736,614, Final Office Action mailed May 6, 2015", 21 pgs.

"U.S. Appl. No. 13/736,614, Final Office Action mailed Dec. 7, 2015", 19 pgs.

"U.S. Appl. No. 13/736,614, Non Final Office Action mailed Sep. 22, 2015", 19 pgs.

"U.S. Appl. No. 13/736,614, Response filed Apr. 6, 2015 to Non-Final Office Action mailed Jan. 5, 2015", 15 pgs.

"U.S. Appl. No. 13/736,614, Response filed Jul. 6, 2015 to Final Office Action mailed May 6, 2015", 15 pgs.

"U.S. Appl. No. 13/736,614, Response filed Nov. 25, 2015 to Non Final Office Action mailed Sep. 22, 2015", 12 pgs.

"U.S. Appl. No. 13/736,614, Non Final Office Action mailed Jan. 5, 2015", 20 pgs.

"U.S. Appl. No. 13/736,614, Response filed Nov. 4, 2014 to Final Office Action mailed Aug. 4, 2014", 12 pgs.

"U.S. Appl. No. 13/736,614, Final Office Action mailed Aug. 4, 2014", 13 pgs.

"U.S. Appl. No. 13/736,614, Non Final Office Action mailed Apr. 21, 2014", 13 pgs.

"U.S. Appl. No. 13/736,614, Response filed Jul. 21, 2014 to Non-Final Office Action mailed Apr. 21, 2014", 11 pgs.

"International Application Serial No. PCT/US2013/020666, International Preliminary Report on Patentability mailed Jul. 24, 2014", 9 pgs.

"International Application Serial No. PCT/US2013/020666, International Search Report mailed May 8, 2013", 4 pgs.

"International Application Serial No. PCT/US2013/020666, Written Opinion mailed May 8, 2013", 7 pgs.

"European Application Serial No. 13701883.4, Response filed Mar. 24, 2016 to Communication Pursuant to Article 94(3) EPC mailed Sep. 16, 2015", 7 pgs.

"European Application Serial No. 13701883.4, Communication Pursuant to Article 94(3) EPC mailed Sep. 16, 2015", 4 pgs.

"European Application Serial No. 13701883.4, Response filed Mar. 2, 2015 to Communication pursuant to Rules 161(1) and 162 EPC mailed Aug. 13, 2014", 11 pgs.

* cited by examiner

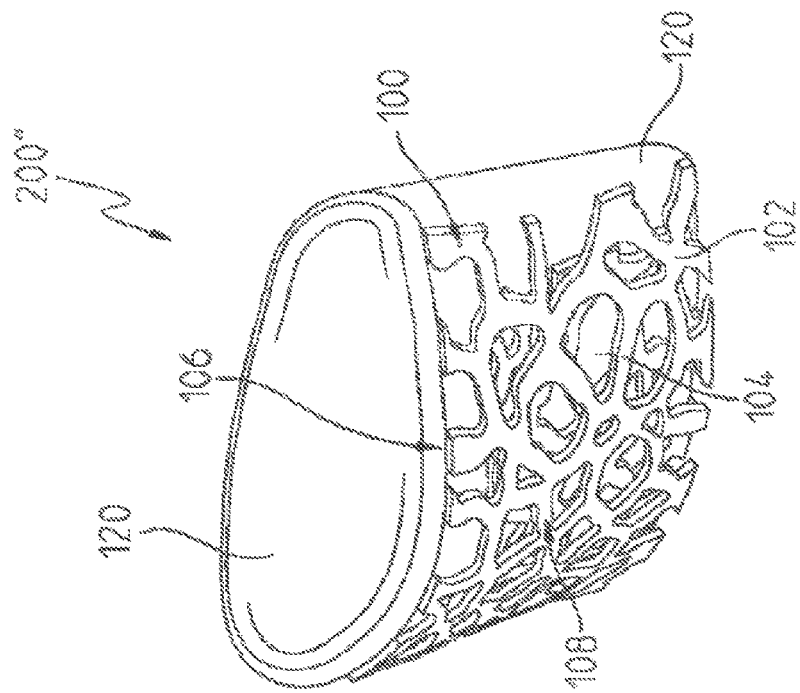
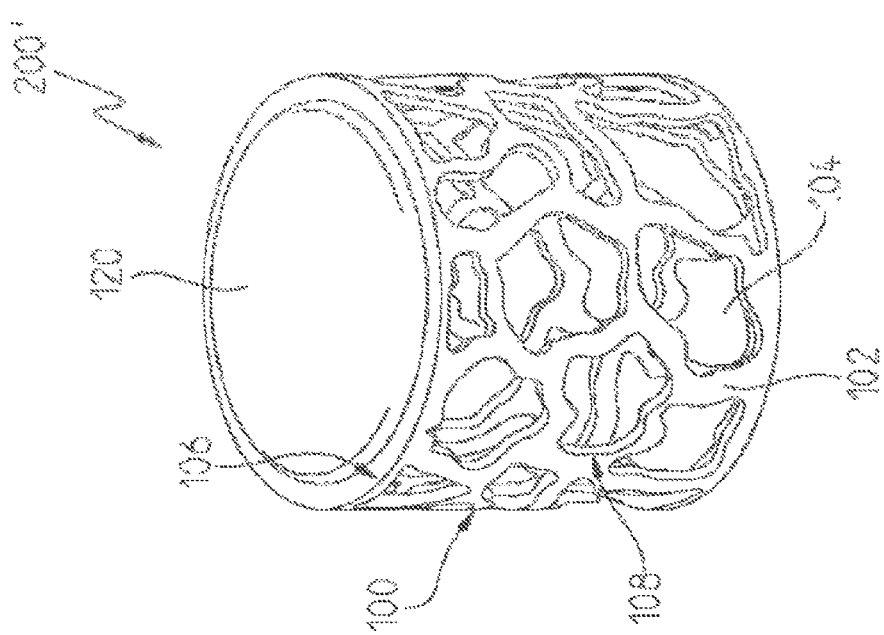

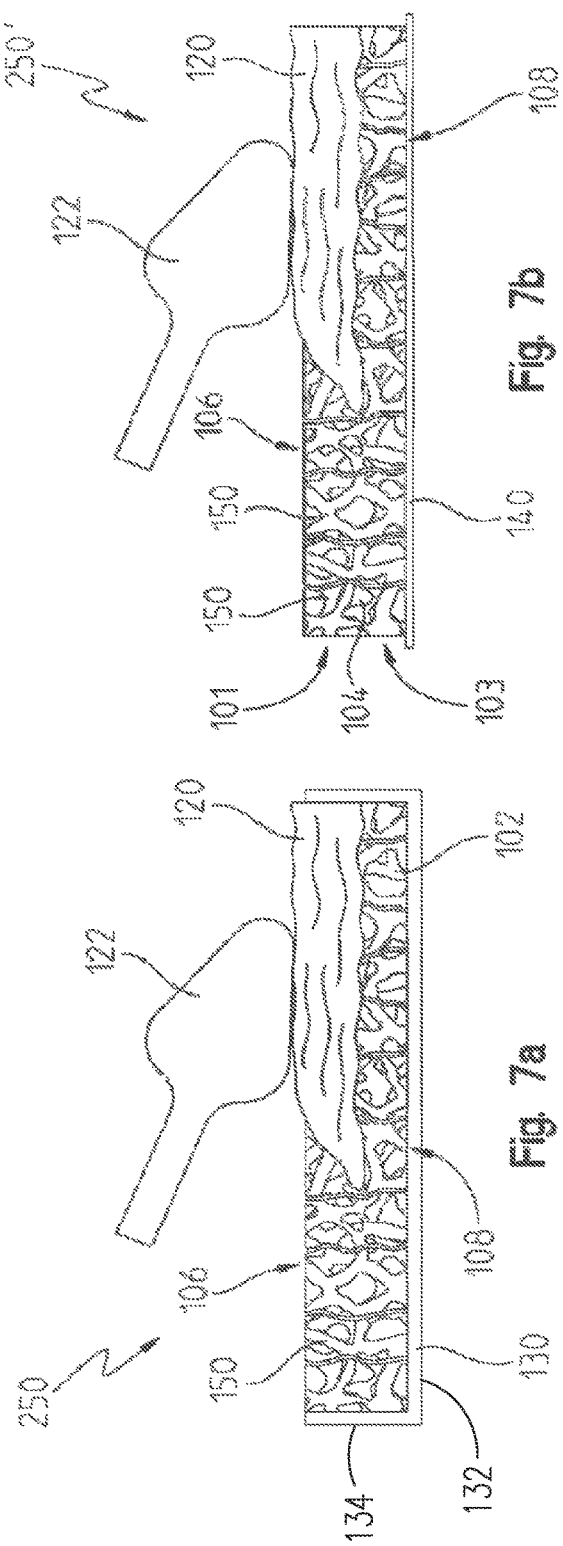
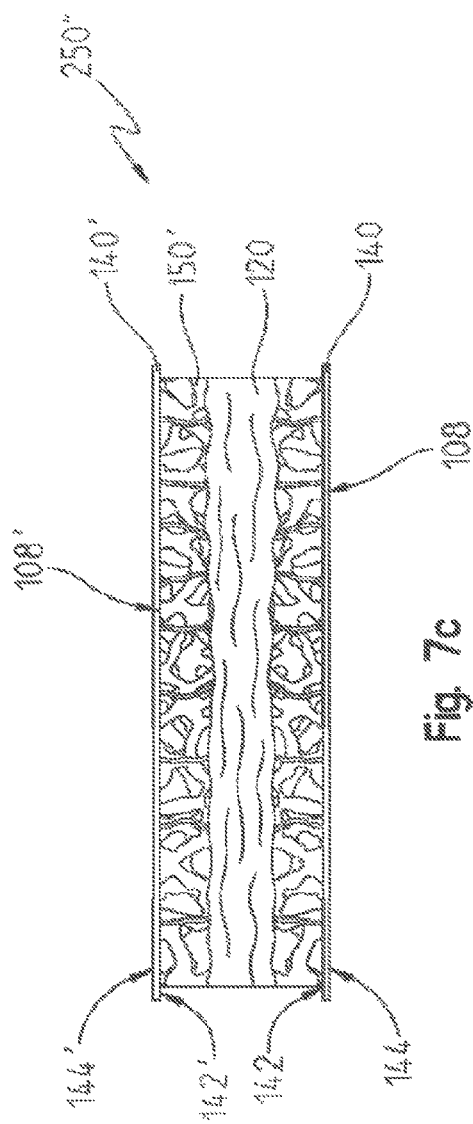

POROUS METAL IMPLANTS WITH BONE CEMENT

CLAIM OF PRIORITY

This application is a continuation of U.S. patent application Ser. No. 13/736,614, filed on Jan. 8, 2013 which claims the benefit of U.S. Provisional Patent Application Ser. No. 61/584,463, filed on Jan. 9, 2012, the benefit of priority of each of which is claimed hereby, and each of which are incorporated by reference herein in its entirety.

BACKGROUND

1. Field of the Disclosure

The present invention relates to filling voids in bones. More particularly, the present invention relates to orthopaedic implants having a porous metal portion and bone cement portion for filling voids in bones, and methods for using the same.

2. Description of the Related Art

Bone voids may result for a number of reasons. For example, joint injuries or disease may result in the formation of defects and voids in a bone. Additionally, many orthopaedic surgical procedures require drilling into bone, thereby creating bone voids. Further, the locations at which bone voids occur, and the size of bone voids, are patient specific. Thus, the use of standard implants for filling bone voids may not be possible.

SUMMARY

The present disclosure provides a porous metal implant with bone cement for filling voids in bones.

According to an embodiment of the present disclosure, an orthopaedic implant for filing a bone void is provided. The orthopaedic implant comprises an open porous metal portion having a first porous layer opposite a second porous layer, and a curable fixative portion at least partially disposed over an area of the first porous layer. The curable fixative is also at least partially disposed within a portion of the first porous layer.

According to another embodiment of the present disclosure, the first porous layer further comprises a plurality of first pores having a first nominal pore diameter for contacting tissue and the second porous layer further comprises a plurality of second pores having a second nominal pore diameter.

According to yet another embodiment of the present disclosure, the first porous layer comprises a thickness of between one and ten first pore diameters and the second porous layer comprises a thickness of between one and ten second pore diameters.

BRIEF DESCRIPTION OF THE DRAWINGS

The above-mentioned and other features and advantages of this disclosure, and the manner of attaining them, will become more apparent and the disclosure itself will be better understood by reference to the following description of embodiments of the disclosure taken in conjunction with the accompanying drawings, wherein:

FIG. 5*a* is an enlarged perspective view of an embodiment of an orthopaedic implant according to the instant disclosure having an open porous metal encircling a formed portion of bone cement;

FIG. 5*b* is an enlarged perspective view of another embodiment of an orthopaedic implant according to the instant disclosure having an open porous metal partially encircling a formed portion of bone cement;

FIG. 7*a* is a cross-sectional view of the orthopaedic implant of FIG. 6 showing the application of bone cement to the first surface region of the plurality of open porous metal fragments positioned within a support form;

FIG. 7*b* is another cross-sectional view of another embodiment of an orthopaedic implant according to the instant disclosure, illustrating the application of bone cement to the first surface region of a plurality of open porous metal fragments positioned on an adhesive surface of a backing film;

FIG. 7*c* is an cross-sectional view of another embodiment of an orthopaedic implant according to the instant disclosure, illustrating a first and second plurality of open porous metal fragments spaced apart by bone cement, each plurality of metal fragments having a first surface region contacting bone cement and a second surface region positioned on an adhesive surface of a backing film;

Corresponding reference characters indicate corresponding parts throughout the several views. The exemplifications set out herein illustrate exemplary embodiments of the disclosure and such exemplifications are not to be construed as limiting the scope of the disclosure in any manner.

DETAILED DESCRIPTION

The present disclosure provides orthopaedic implants having an open porous metal portion together with a curable fixative, such as bone cement. Advantageously, the orthopaedic implants disclosed herein may be sized and shaped by a medical professional at the time of surgery in a custom manner, in order to accommodate patient specific needs.

Figure 1:
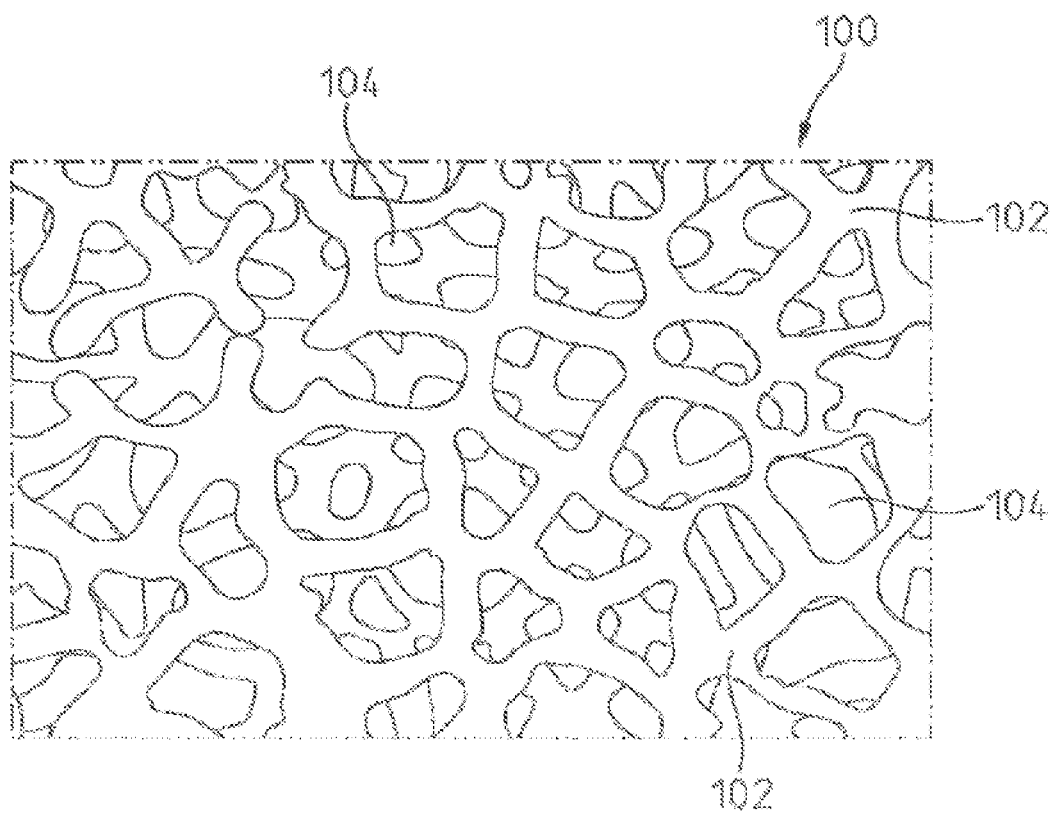
FIG. 1 is an enlarged view of the structure of an open porous metal according to the instant disclosure.

With reference to FIG. 1, an illustrative embodiment of open porous metal 100 is depicted. As shown, open porous metal 100 includes a plurality of ligaments 102 defining a plurality of highly interconnected, three-dimensional open spaces or pores 104 therebetween. Also, the pores 104 of open porous metal 100 may form a matrix of continuous channels having no dead ends between ligaments 102. Therefore, it is within the scope of orthopaedic implant 200 that open porous metal 100 may include up to 75%-85% or more void space therein. As such, open porous metal 100 may be a lightweight, strong porous structure which is substantially uniform and consistent in composition.

According to the instant disclosure, embodiments of open porous metal 100 may have a porosity of as low as 55%, 65%, or 75% or as high as 80%, 85%, or 90%. An example of such an open porous metal 100, comprising a biocompatible metal, is produced using Trabecular Metal™ Technology generally available from Zimmer, Inc., of Warsaw, Ind., Trabecular Metafim is a trademark of Zimmer, Inc. Such an open porous metal 100 may be formed from a reticulated vitreous carbon foam substrate which is infiltrated and coated with a biocompatible metal, such as tantalum, by a chemical vapor deposition ("CND") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used. Further, other biocompatible metals, such as titanium, a titanium alloy, cobalt chromium, cobalt chromium molybdenum, tantalum, or a tantalum alloy may also be used.

Additionally, embodiments of open porous metal 100 may comprise a Ti-6Al-4V ELI alloy, such as Tivanium® Alloy which is available from Zimmer, Inc., of Warsaw, Ind. Tivanium® is a registered trademark of Zimmer, Inc. Open porous metal 100 may also comprise a fiber metal pad or a sintered metal layer, such as a CSTi™, Cancellous-Structured Titanium™ coating or layer, for example, CSTi™ porous layers are manufactured by Zimmer, Inc., of Warsaw, Ind. CSTi™ is a trademark of Zimmer, Inc.

In other embodiments, open porous metal 100 may comprise an open cell polyurethane foam substrate coated with Ti-6Al-4V alloy using a low temperature arc vapor deposition process. Ti-6Al-4V beads may then be sintered to the surface of the Ti-6Al-4V-coated polyurethane foam substrate. Additionally, another embodiment of open porous metal 100 may comprise a metal substrate combined with a Ti-6AL-4V powder and a ceramic material, which is sintered under heat and pressure. The ceramic particles may thereafter be removed leaving voids, or pores, in the substrate. Open porous metal 100 may also comprise a Ti-6Al-4V powder which has been suspended in a liquid and infiltrated and coated on the surface of a polyurethane substrate. The Ti-6Al-4V coating may then be sintered to form a porous metal structure mimicking the polyurethane foam substrate. Further, another embodiment of open porous metal 100 may comprise a porous metal substrate having particles, comprising altered geometries, which are sintered to a plurality of outer layers of the metal substrate.

Further, other embodiments of open porous metal 100 may comprise a porous collagen scaffold core with calcium phosphate embedded therein. Still other embodiments of open porous metal 100 may include a type 1 collagen core matrix with bone and blood fragments embedded therein. In yet other embodiments, open porous metal 100 may comprise a synthetic hydroxylapatite scaffold core having an external negative charge and having various growth factors (e.g., osteocytic and fibrocytic growth factors) embedded therein. Still other embodiments of open porous metal 100 within the scope of the present disclosure may include a resorbable inorganic calcium phosphate scaffold core with human fibrin embedded therein. Additionally, some embodiments of open porous metal 100 may comprise a synthetic biocompatible calcium sulfate scaffold core.

Open porous metal 100 may also be fabricated such that it comprises a variety of densities. In particular, as discussed in the above-incorporated U.S. Pat. No. 5,282,861, open porous metal 100 may be fabricated to virtually any desired density, porosity, and pore size. Thus, open porous metal 100 can be matched with surrounding natural tissue in order to provide an improved matrix for tissue ingrowth and mineralization, thereby aiding in fixation of open porous metal 100 to the surrounding natural tissue.

Additionally, according to the instant disclosure, open porous metal 100 may be fabricated to comprise substantially uniform porosity, density, and/or pore size throughout, or to comprise at least one of pore size, porosity, and/or density being varied. For example, according to embodiments of orthopaedic implant 200 disclosed herein, open porous metal 100 may have a different pore size and/or porosity at different regions or layers of open porous metal 100. The ability to selectively tailor the structural properties of open porous metal 100, enables tailoring of open porous metal 100 for distributing stress loads throughout the surrounding tissue and tissue ingrown within open porous metal 100.

Figure 2:
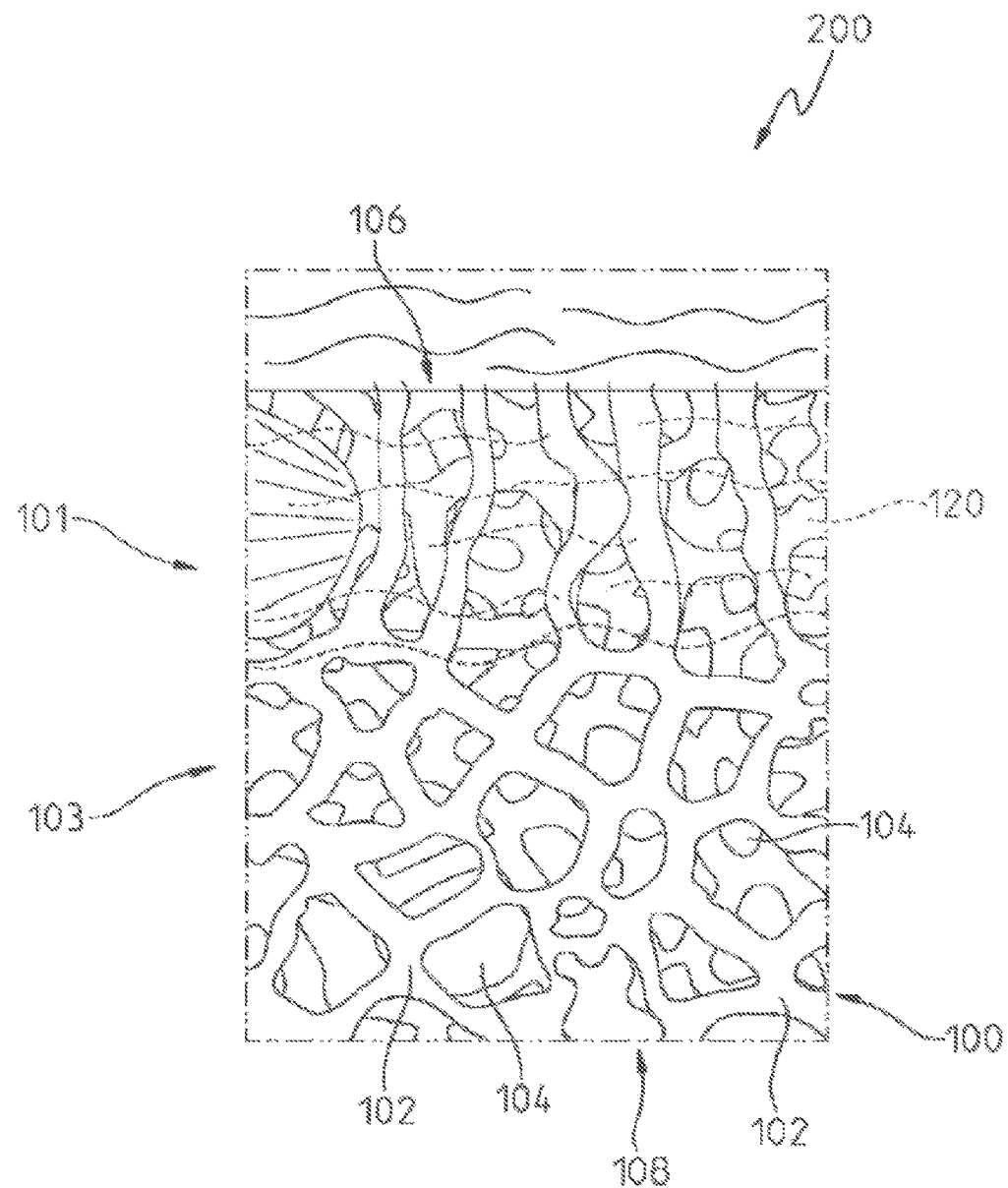
FIG. 2 is a cross-sectional view of the open porous metal of FIG. 1 having bone cement applied at the first surface region and being received within the plurality of pores of the open porous metal to a depth of approximately one-half the thickness of the open porous metal.

With reference to FIG. 2, an illustrative embodiment of orthopaedic implant 200 is depicted. As shown in FIG. 2, orthopaedic implant 200 comprises open porous metal 100 and bone cement 120. According to embodiments of orthopaedic implant 200 disclosed herein, open porous metal 100 may comprise a porous metallic sheet, being relatively thin (e.g., having a thickness of four to ten pore diameters) and may also boat least partially flexible or pliable. Thus, open porous metal 100 may be shaped and sized according to a particular application. For example, a surgeon may shape, cut, bend, or trim open porous metal 100 to any desired custom size and shape in order to meet a particular need. Shaping and sizing of open porous metal 100 may occur prior to, or after bone cement 120 is applied to open porous metal 100. As such, orthopaedic implant 200 may be used to fill unique bone voids having different shapes and sizes and occurring at various patient specific locations.

Figure 4B:
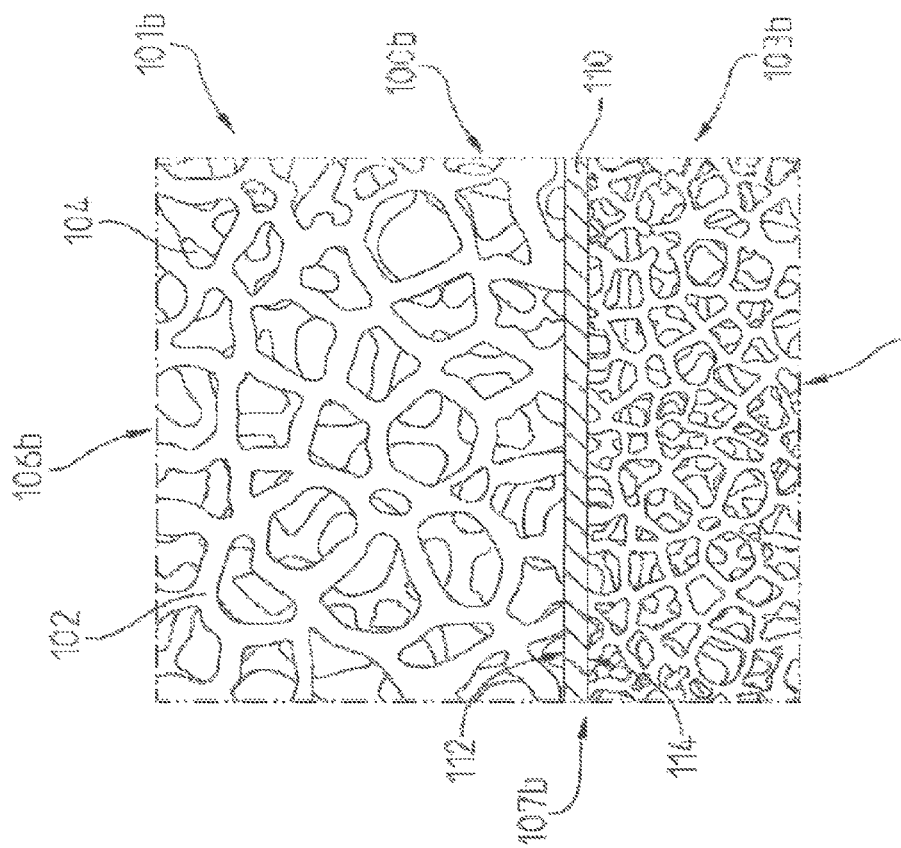
FIG. 4*b* is another cross-sectional view of an embodiment of an open porous metal having larger pore sizes proximate the first surface region and smaller pore sizes proximate the second surface region with an affixation substrate separating the plurality of pores proximate the first surface region from the of pores proximate the second surface region.
Figure 4A:
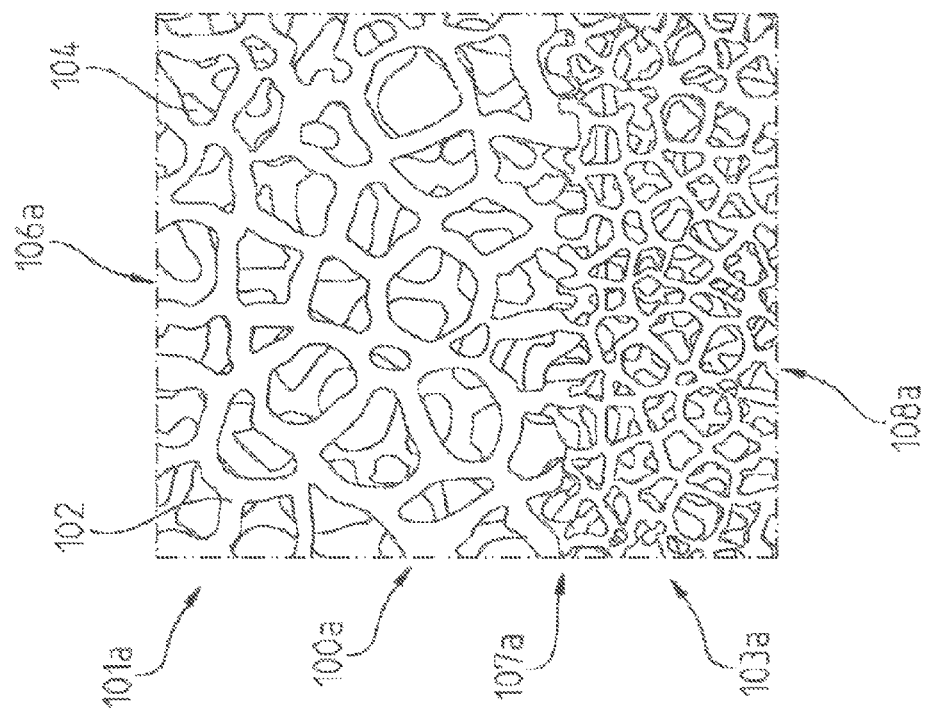
FIG. 4*a* is a cross-sectional view of an embodiment of an open porous metal having larger pore sizes proximate the first surface region and smaller pore sizes proximate the second surface region.

With reference to FIGS. 4a and 4b, two embodiments of open porous metal 100, both having regions comprising different pore sizes and porosity, are shown. Referring specifically to FIG. 4a, open porous metal 100a comprises first layer 101a, second layer 103a, first surface region 106a, intermediate region 107a, and second surface region 108a. As illustrated, the nominal pore size of open porous metal 100a is relatively greater in first layer 101a and at first surface region 106a as compared to second layer 103a and second surface region 108a. In some embodiments of open porous metal 100*a*, the alteration in pore size and porosity may gradually occur between first layer 101*a* and second layer 103*a* to form a gradually increasing or decreasing pore size gradient. In other embodiments of open porous metal 100*a*, the change in pore size and porosity may be defined and localized at interface region 107*a*, such as illustrated in FIG. 4*a*.

Embodiments of open porous metal 100*a*, such as illustrated in FIG. 4*a*, may comprise a reticulated vitreous carbon (RVC) substrate of a uniform pore size having biocompatible metal, such as tantalum, infiltrated and coated thereon such as described in the above-incorporated U.S. Pat. No. 5,282,861. According to the instant disclosure, in order to form a porous metal having varying pore sizes, a greater amount of the biocompatible metal may be infiltrated and coated on the carbon substrate in the second layer than in the first layer, resulting in the second layer having decreased pore size. This may be accomplished by masking a portion of the carbon substrate during the infiltration and deposition process, or, following an initial extent of infiltration and deposition of the metal, by at least partially filling a sacrificial material into the pores of one of the layers, followed by carrying out further infiltration and deposition of the metal into the pores of the other layer and then removing the sacrificial material.

Another embodiment of open porous metal 100*a* may comprise two or more different carbon substrates, each comprising different pore size and porosity. The two or more carbon substrates may then be diffusion bonded together, for example at interface region 107*a*, using applied pressure at an elevated temperature for an appreciable period of time. Further, the two or more carbon substrates may be combined through an infiltration and deposition welding process, in which the substrates, perhaps following an initial extent of infiltration and deposition of the metal into the substrates as separate components, are held against one another followed by exposing the combined substrate to a further extent of infiltration and deposition of the metal to concurrently coat and thereby fuse the substrates together. In a further embodiment, the substrates may be fused together by a resistance welding process using localized heat generated through electric resistance.

FIG. 4*b* provides another illustrative embodiment of open porous metal 100 having regions comprising different pore sizes and porosity. As shown in 4*b*, open porous metal 100*b* comprises first layer 101*b*, second layer 103*b*, first surface region 106*b*, intermediate region 107*b*, and second surface region 108*b*. Intermediate region 107*b* of open porous metal 100*b* comprises affixation substrate 110 positioned between first layer 101*b* having greater pore size and decreased porosity, and second layer 103*b* having smaller pore size and greater porosity. As shown, first layer 101*b* is affixed to first surface 112 or affixation substrate 110 and second layer 103*b* is affixed to second surface 114 of affixation substrate 110. Similar to the above-described embodiment of FIG. 4*a*, first layer 101*b* and second layer 103*b* may be diffusion bonded to first surface 112 and second surface 114 of affixation plate 110, respectively, using applied pressure at an elevated temperature for an appreciable period of time. Further, first layer 101*b* and second layer 103*b* may also be affixed to first surface 112 and second surface 114 of affixation plate 110, respectively, by the infiltration and deposition welding described above, or through resistance welding using heat generated through electric resistance.

Figure 3:
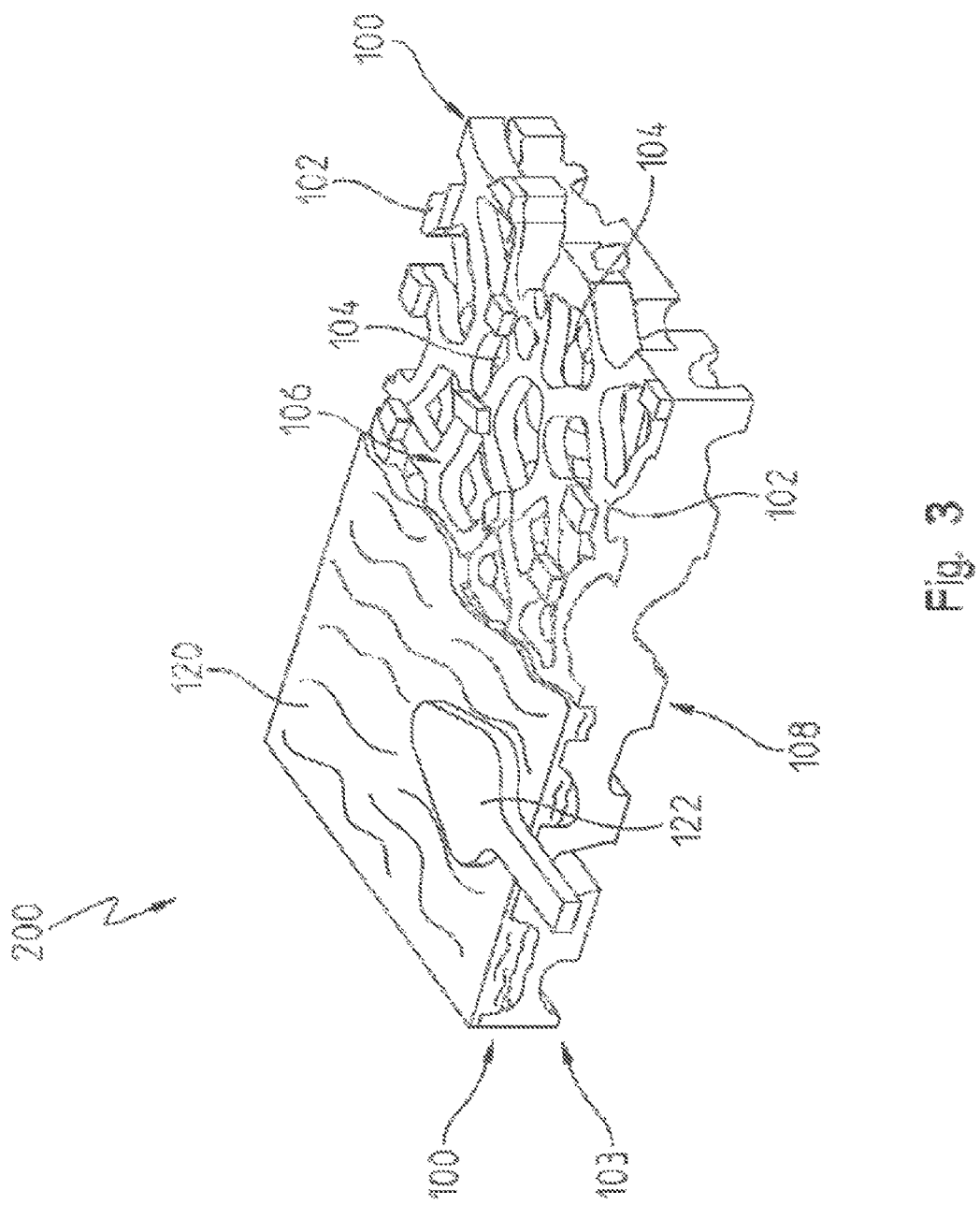
FIG. 3 is a perspective view of the open porous metal of FIGS. 1 and 2 showing the application of bone cement to the first surface region of the open porous metal.

With reference to FIG. 3, preparation of an illustrative embodiment of orthopaedic implant 200 is shown. According to the embodiment presented in FIG. 3, bone cement 120 is applied, using applicator 122, to first surface region 106 of open porous metal 100. As intended herein, applicator 122 refers to manual devices, such as knives, scrapers, brush, depressors, swabs, and the like. It is also within the scope of the preparation of orthopaedic implant 200 that applicator 122 may include an automated applicator capable of mechanically applying and/or spreading bone cement 120 onto first porous surface 106 of plurality of fragments 150. Further, bone cement 120 may be applied to orthopaedic implant 200 manually, for example by hand.

Also, as used herein, bone cement 120 refers to a curable fixative capable of affixing implants to bone and/or replacing or remodeling lost bone. For example, poly(methyl methacrylate) ("PMMA") is one compound capable of comprising bone cement 120. Bone cement 120 may also include other moldable materials, such as biodegradable polymers, for example, polyhydroxyalkanoate. Additionally, bone cement 120 will typically be capable of bonding to one of, or both of, bone or an implant. Further, bone cement 120, according to the instant disclosure, may comprise a powder capable of being mixed with a liquid, or a liquid or gel which hardens into a solid material.

Bone cement 120 is applied to orthopaedic implant 200 such that it is received within pores 104 of first layer 101 proximal first surface region 106. Typically, bone cement 120 will be applied in a form in which bone cement 120 is not fully cured, i.e., is relatively thick and viscous but not fully hardened. As shown in the illustrative embodiment of orthopaedic implant 200 of FIG. 2, bone cement 120 may be received within pores 104 of first layer 101 up to a depth of approximately one half the depth (in pore diameters) of open porous metal 100. In other embodiments of orthopaedic implant 200, bone cement 120 may be received within pores 104 of first layer 101 up to a depth of approximately 10 pore diameters. In yet other embodiments of orthopaedic implant 200, bone cement 120 may be received within pores 104 of first layer 101 up to a depth of approximately 4-6 pore diameters. It is also within the scope of the instant disclosure that bone cement 120 be received within pores 104 of first layer 101 at a depth of less than four pore diameters. The receipt of bone cement 120 within pores 104 of open porous metal 100 creates a strong, rigid fixation of bone cement 120 to open porous metal 100 following curing of the bone cement 120.

Also, as shown in FIG. 2, bone cement 120 is not applied to second surface region 108 of orthopaedic implant 200. Further, bone cement 120 applied to first surface region 106 is not received within plurality of pores 104 of first layer 101 such that bone cement 120 extends through open porous metal 100 to the plurality of pores 104 of second layer 103 and second surface region 108.

As referenced above, second surface region 108 provides a tissue contacting surface of orthopaedic implant 200 which allows for tissue ingrowth and mineralization within the plurality of pores 104 proximal second surface region 108. Although not specifically illustrated in the embodiment of orthopaedic implant 200 shown in FIG. 2, it should be understood that orthopaedic implant 200 may comprise open porous metal 100 having any of density, porosity, and pore size at second surface region 108 which differs from the density, porosity, and pore size at first surface region 106 (e.g., as depicted in FIGS. 4*a* and 4*b*). As such, open porous metal 100 may be fabricated such that first surface region 106 includes pores 104 of a relatively larger size in order to facilitate receipt of bone cement 120, and second surface region 108 may include pores 104 of a relatively smaller size that are more tailored to facilitate ingrowth and/or mineralization of orthopedic implant 200 with a specific tissue.

Additionally, it is within the scope of orthopaedic implant 200 that open porous metal 100 may be impregnated with and/or coated with biologically active agents. Suitable biologically active agents include, for example, antibiotics to reduce the potential for infection and to promote healing, and growth factors to promote bone and/or soft tissue ingrowth into open porous metal 100 comprising a tissue contacting surface of orthopaedic implant 200. By way of example, second surface region 108 may be impregnated with osteocytic growth factors for promoting bone ingrowth within the plurality of pores 104 proximal second surface region 108. In some embodiments, strontium may be combined with the orthopedic implants disclosed herein as an active agent to promote bone growth.

Referring to FIGS. 5a and 5b, additional illustrative embodiments of orthopaedic implant 200 are shown. According to FIG. 5a, open porous metal 100 may be applied to, or pressed into, a formed portion of bone cement 120, such that open porous metal 100 encircles (or in some instances encases) bone cement 120. FIG. 5b presents an illustrative embodiment of orthopaedic implant 200" having open porous metal 100 applied to another formed portion of bone cement 120, such that open porous metal 100 partially encircles the bone cement 120 portion. In both embodiments of orthopaedic implant 200', 200" presented in FIGS. 5a and 5b, open porous metal 100 may comprise a relatively thin metallic, malleable sheet. As shown, open porous metal 100 is pressed into bone cement 120 such that bone cement 120 is received within the plurality of pores 104 approximately one-half the depth of the sheet of open porous metal 100. As such, a surgeon may custom form bone cement 120 of orthopaedic implants 200', 200" to meet patient specific needs by shaping and sizing bone cement 120 and the sheet of open porous metal 100 during the surgical procedure.

Additionally, as shown in FIGS. 5a and 5b, open porous metal 100 is applied to bone cement 120 such that first surface region 106 contacts bone cement 120 and bone cement 120 is received within the plurality of pores 104 proximal first surface region 106 similar to the embodiments of orthopaedic implant 200 presented in FIGS. 2 and 3. Also, bone cement 120 is not applied to second surface region 108 of orthopaedic implants 200', 200", and bone cement 120 received within the plurality of pores 104 proximal first surface region 106 does not extend through open porous metal 100 to the plurality of pores 104 proximal second surface region 108. In this manner, the pores 104 of second surface region 108, which may be relatively smatter than the pores 104 of first surface region 106 and tailored in size to facilitate tissue ingrowth, are exposed to surrounding bone and/or soft tissue to facilitate tissue ingrowth and anchoring of orthopaedic implants 200', 200".

Figure 6:
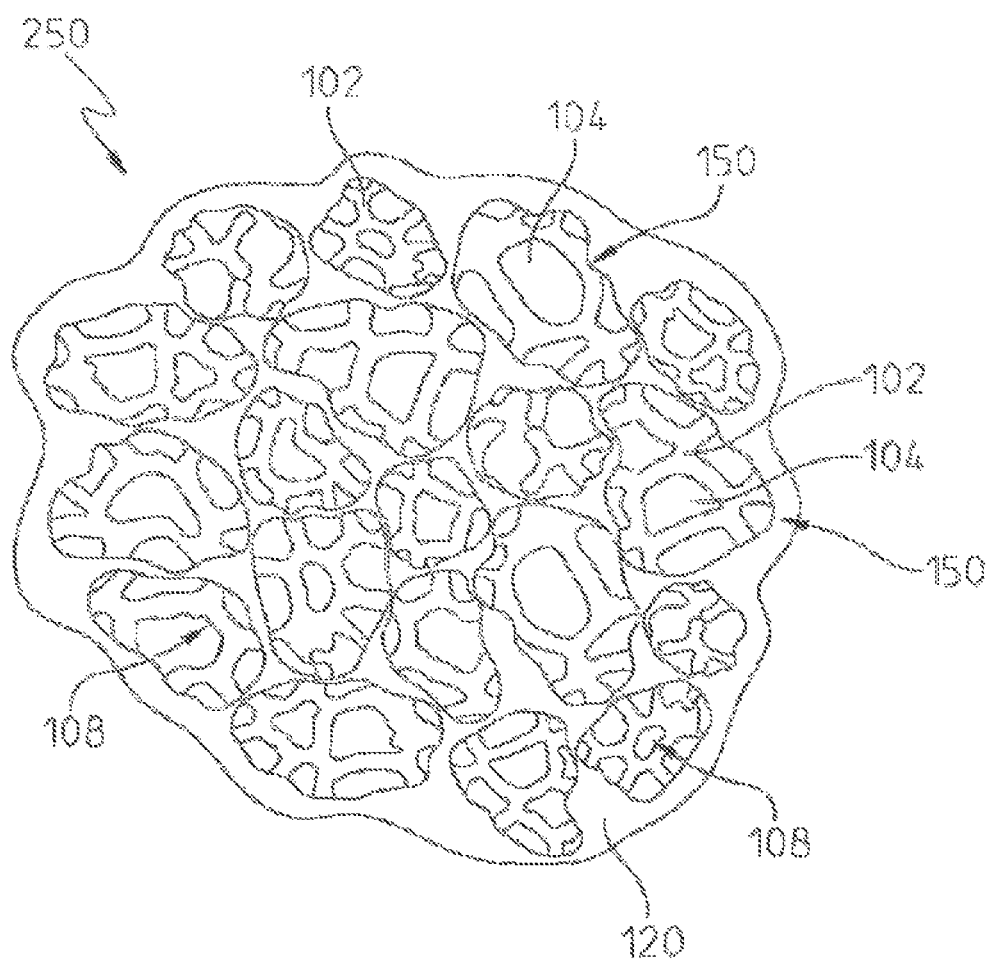
FIG. 6 is an enlarged view of an embodiment of an orthopaedic implant according to the instant disclosure having a plurality of open porous metal fragments with bone cement applied to the first surface region.

Referring to FIGS. 6, 7a, 7b, and 7c, illustrative embodiments of orthopaedic implant 250 are shown. Embodiments of orthopaedic implant 250 may include any of the characteristics and features discussed in regard to orthopaedic implant 200. In addition to the features discussed with regard to orthopaedic implant 200, embodiments of orthopaedic implant 250, such as illustrated in FIG. 6, comprise a plurality of fragments 150. According to the instant disclosure, the plurality of fragments 150 comprise fragments of open porous metal 100, as disclosed herein, and may be formed in various sizes and shapes. In general, however, where orthopaedic implant 250 is relatively thin and sheet-like in shape, the plurality of fragments 150 will together typically have substantially the same depth. Additionally, according to an embodiment of orthopaedic implant 250, the plurality of fragments 150 may comprise at least one of pore size, density, and porosity which is either uniform or varies from first surface region 106 to second surface region 108 (as shown in FIGS. 4a and 4b).

With reference to FIGS. 7a, 7b, and 7c, illustrative embodiments of orthopaedic implants 250, 250', and 250", respectively, are depicted.

According to the instant disclosure, preparation of the embodiments of orthopaedic implants 250, 250', and 250" may comprise a sheet of open porous metal 100 being placed within form 130 (FIG. 7a), or adhered to backing film 140 (FIGS. 7b and 7c), and then shattered. For example, a sheet of open porous metal 100 may be frozen by exposure to liquid nitrogen prior to being placed in form 130 (FIG. 7a) or prior to or after being adhered to backing film 140 (FIGS. 7b and 7c). Once the frozen sheet of open porous metal 100 is within form 130 (FIG. 7a) or adhered to backing film 140 (FIGS. 7b and 7c), a force may be applied to the sheet of open porous metal 100, thereby causing the sheet of open porous metal 100 to break into a plurality of fragments 150.

Additionally, although not depicted, each of the plurality of fragments 150 may be prepared individually, according to the fabrication of open porous metal 100 discussed in the above-incorporated U.S. Pat. No. 5,282,861. In such case, the plurality of fragments 150 may be positioned within form 130 (FIG. 7a) or adhered to backing film 140 (FIGS. 7b and 7c) prior to applying bone cement 120.

According to the illustrative embodiments of orthopaedic implant 250 depicted in FIGS. 6, 7a, 7b, and 7c, bone cement 120 is applied to first surface region 106 of the plurality of fragments 150 and is received within the plurality of pores 104 proximal first surface region 106. Bone cement 120, however, is not applied to second surface region 108 of the plurality of fragments 150 illustrated in FIGS. 6, 7a, 7b, and 7c. Also, bone cement 120 applied to first surface region 106 is not received within the plurality of pores 104 proximal first surface region 106 such that it extends through open porous metal 100 to the plurality of pores 104 proximal second surface region 108.

With reference to FIGS. 7a and 7b, an illustrative embodiment of an applicator 122 is depicted. According to the instant disclosure, applicator 122 may he used for applying bone cement 120 to first surface region 106 of plurality of fragments 150. As intended herein, applicator 122 refers to manual devices, such as knives, scrapers, brush, depressors, swabs, and the like. It is also within the scope of the instant disclosure that applicator 122 may include an automated applicator capable of mechanically applying and/or spreading bone cement 120 onto first surface region 106 of plurality of fragments 150. Further, bone cement 120 may be applied to orthopaedic implant 250 manually, for example, by hand.

Referring specifically to FIG. 7a, a plurality of fragments 150 of orthopaedic implant 250 are positioned within form 130. Also illustrated, sides 134 of form 130 provide support which aides in holding plurality of fragments 150 in position during the process of applying bone cement 120 (shown being applied using applicator 122). Form 130 includes bottom 132 and sides 134, and may be comprised of a transparent material, thereby aiding in monitoring the application of bone cement 120. Additionally, according to the instant disclosure, form 130 may comprise a disposable material capable of being removed (e.g., peeled or torn away) from orthopaedic implant 250 upon application of bone cement 120. Removal of form 130 from plurality of fragments 150 thereby provides an implantable orthopaedic implant similar to orthopaedic implant 250 exemplified in FIG. 6.

With reference to FIG. 7b, an exemplary embodiment of orthopaedic implant 250' is depicted. As shown, second surface region 108 of each of a plurality of fragments 150 of orthopaedic implant 250' are positioned in contact with adhesive surface 142 of backing film 140. According to the instant disclosure, backing film 140 aides in holding the plurality of fragments 150 in position during the process of applying bone cement 120 (shown being applied using applicator 122) to first surface region 106. Following the application of bone cement 120 to the plurality of fragments 150, backing film 140 may be removed, thereby exposing the pores of the surface region adjacent backing film 140 to provide an implantable orthopaedic implant similar to orthopaedic implant 250 exemplified in FIG. 6.

Referring to FIG. 7c, an exemplary embodiment of orthopaedic implant 250" is exemplified. According to the illustrative embodiment orthopaedic implant 250" presented in FIG. 7c, orthopaedic implant 250" includes a first and a second plurality of fragments 150, 150'. As shown, second surface region 108 of the first plurality of fragments 150 is positioned in contact with adhesive surface 142 of backing film 140 and second porous surface 108' of the second plurality of fragments 150' is positioned in contact with adhesive surface 142' of a second backing film 140'. Bone cement 120 is then applied to first surface region 106 of both the first and second plurality of fragments 150, 150".

As shown in FIG. 7c, once bone cement 120 has been applied to the first surface region 106, 106' of the first and second plurality of fragments 150, 150', the first and second plurality of fragments 150, 150' are contacted together such that bone cement 120 separates the first surface region 106, of the first plurality of fragments 150, from the first surface region 106' of the second plurality of fragments 150'. Prior to implanting orthopaedic implant 250", backing films 140, 140' are removed from the first and second plurality of fragments 150, 150'. Upon removal of backing films 140, 140', an implantable orthopaedic implant 250" is provided having second surface region 108, of the first plurality of fragments 150, and second surface region 108' wherein the pores of the second plurality of fragments 150' are exposed. As such, when implanted, orthopaedic implant 250" may contact bone, soft tissue, and/or a combination of both at the second surface region 108, 108 of the first and second plurality of fragments 150, 150'.

With reference to FIGS. 7b and 7c, backing film 140 (including backing film 140') may comprise a flexible plastic film, such as tape, a paper film, and/or a metal tape having at least one adhesive surface. It is also within the scope of the orthopaedic implants exemplified in FIG. 7b (250') and FIG. 7c (250") that backing film 140 may comprise a rigid material.

According to the instant disclosure, removal of backing film 140 from the plurality of fragments 150 may be accomplished by peeling away backing film 140 from second surface region 108. For example, exposed surface 144 of backing film 140 may have a tab which can be used for peeling or tearing backing film 140 away from the plurality of fragments 150. Further, removal of backing film 140 may require use of an instrument, such as a surgical pick, to peel or pry backing film 140 away from the plurality of fragments 150.

Further, the illustrative embodiments of orthopaedic implant 250 (exemplified in FIGS. 6, 7a, 7b, and 7c), are capable of being customized in shape, size, depth, and orientation for filling bone voids of varying sizes and shapes. According to the instant disclosure, the shape, size, depth, and orientation of orthopaedic implant 250 may be customized immediately prior to implantation into a bone void such as by cutting or trimming to shape, for example, and may be further customized by a surgeon during the actual implantation process. Also, the ability to customize orthopaedic implants 250 allows orthopaedic implants 250 to be used for filling voids at various locations of a bone, and also for securing soft tissue to bone.

Still further, in the embodiments described above in which the porous layer(s) are formed of a plurality of porous metal fragments which are at least partially coated and infiltrated with bone cement, the resulting orthopaedic implant 250 may have an enhanced degree of pliability or flexibility, allowing orthopaedic implant 250 to accommodate and fill bone voids of complex and/or geometrically demanding shapes.

By way of example, one or more of the embodiments of orthopaedic implant 250 disclosed herein may be used for filling a void, in a bone, having an uneven surface and depth. According to the instant disclosure, a surgeon may prepare orthopaedic implant 250 according to any of the preparations depicted in FIGS. 7a, 7b, and 7c. Orthopaedic implant 250 may be implanted in the void such that second porous surface of plurality of fragments contacts the bone lining the void. During implantation into the void, the medical professional may even further modify the shape, form, size, and/or depth of orthopaedic implant 250 in order to fill the void and replace the amount of, and contour of, the lost bone.

Having described various embodiments of orthopaedic implant 200 according to the instant disclosure, applications illustrating and exemplifying uses of embodiments of orthopaedic implant 200 fur filling bone voids will now be described. As used in reference to FIGS. 8-10, unless noted otherwise, reference to orthopaedic implant 200 is intended to represent any and all embodiments of the orthopaedic implants disclosed herein.

Figure 8B:
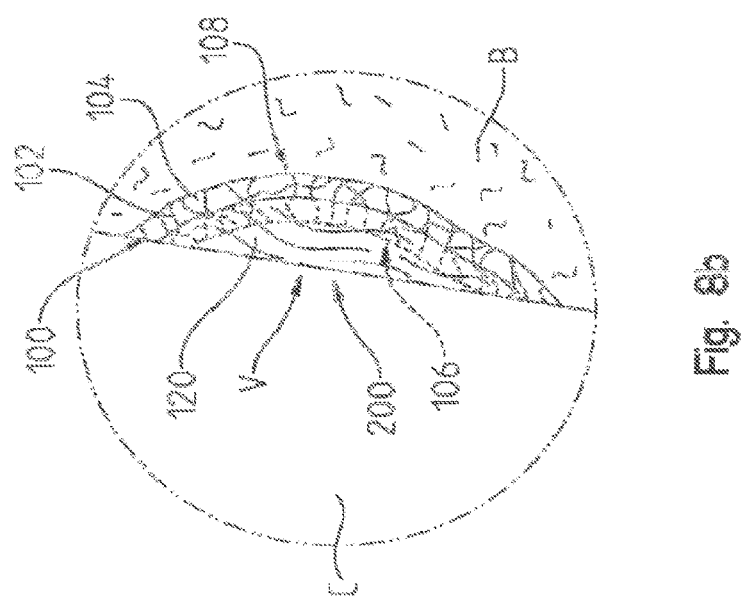
FIG. 8*b* is an enlarged view of the orthopaedic implant implanted within the void of FIG. 8*a*.
Figure 8A:
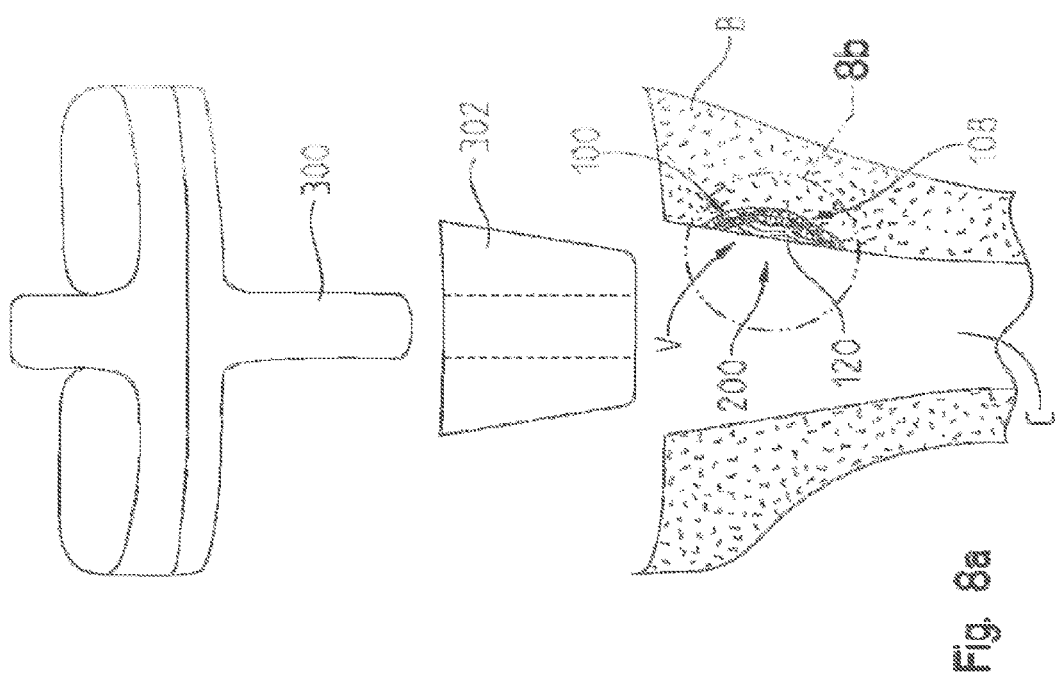
FIG. 8*a* is a cross-sectional view illustrating an orthopaedic implant according to the present disclosure implanted within a void in a tibia.

According to an embodiment of the instant disclosure, illustrated in FIGS. 8a and 8b, orthopaedic implant 200 may be used for filling a void V in a bone B (shown here as a proximal tibia). FIG. 8a shows implantation of tibial tray 300 and augment 302 into the intramedullary canal C of the bone B. As explained above, a void V may occur or form in bone B for any of a number of various reasons. As such, when tibial tray 300 and augment 302 are implanted, orthopaedic implant 200 may be used to fill the void V and reconstruct the natural contour of the intramedullary canal of bone B such that augment 302 may more closely fit) the canal C.

With reference to FIG. 8b, orthopaedic implant 200 is orientated in the void V such that second surface region 108 contacts the bone B lining the void V. As described above, second surface region 108 allows for ingrowth of bone into the plurality of pores 104 proximal second surface region 108, thereby aiding the initial fixation of orthopaedic implant 200 to the bone B.

FIG. 8b also illustrates bone cement 120 which is applied to and received within the pores 104 of first surface region 106 of orthopaedic implant 200 as described above. The bone cement 120 applied to the top of first surface region 106 may then be further shaped (prior to or during implantation of orthopaedic implant 200) to fill the remainder of the void V and reconstruct the contour of the canal C of bone B.

Additionally, according to an embodiment of the instant disclosure augment 302 may itself be formed of open porous metal as disclosed herein. Thus, when augment 302 is implanted into canal C, bone cement 120 applied to first surface region 106 of orthopaedic implant 200 may also be at least partially received within the open porous metal comprising augment 302, thereby aiding in the initial fixation of augment 302.

Figure 9A:
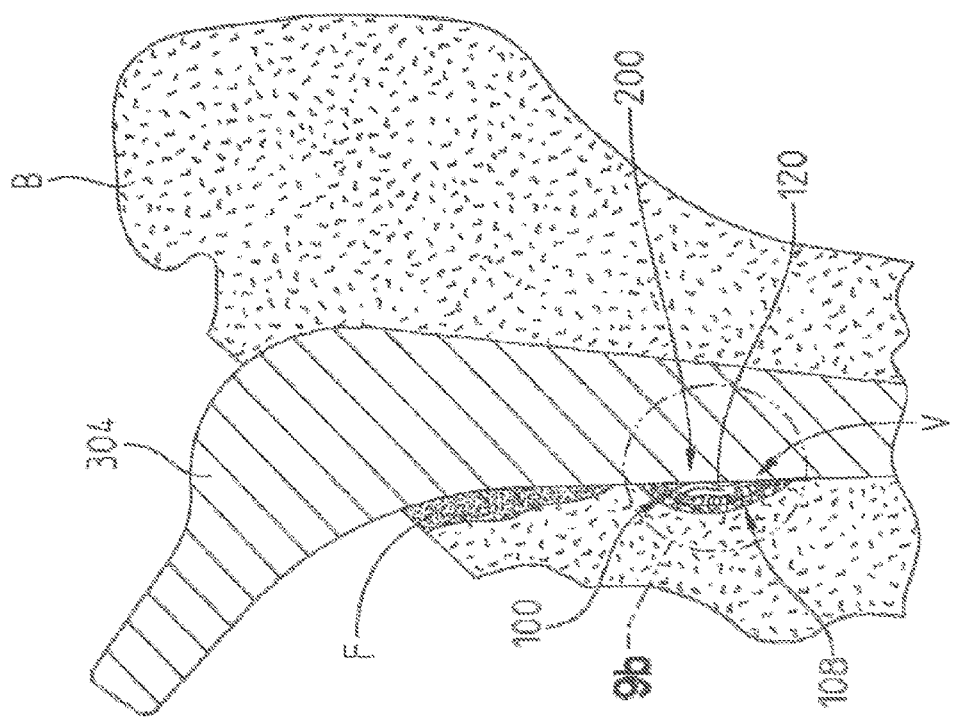
FIG. 9*a* is another cross-sectional view illustrating an orthopaedic implant according to the present disclosure implanted within a void in the femur.
Figure 9B:
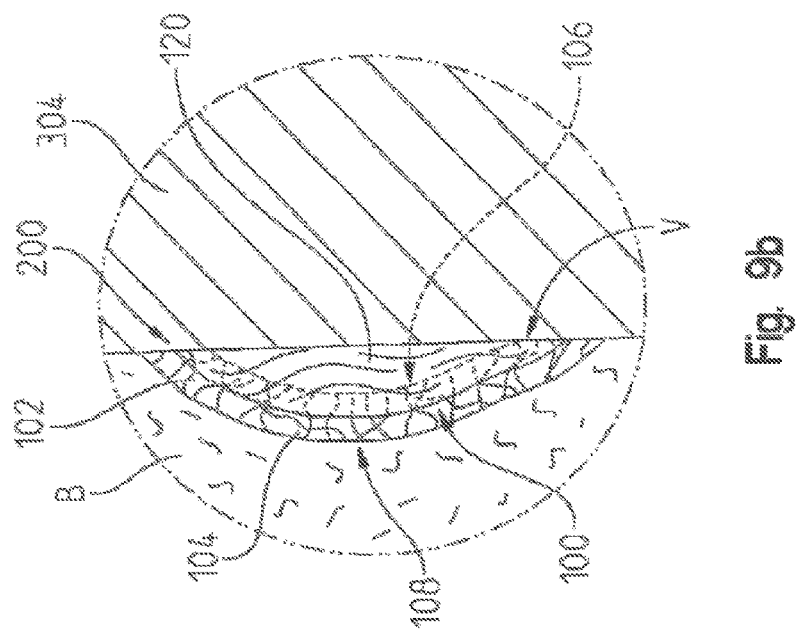
FIG. 9*b* is a enlarged view of the orthopaedic implant implanted within the void of FIG. 9*a*.

Referring to FIGS. 9a and 9b, another illustration of an embodiment of orthopaedic implant 200 being used to fill a void V in a bone B (shown here as a proximal femur) is provided. As shown, orthopaedic implant 200 is used to fill a void V in a bone B prior to implantation of femoral stem 304 into the femoral canal C of bone B.

With reference to FIG. 9b, orthopaedic implant 200 is orientated in the void V such that second surface region 108 contacts the bone B outlining the void V. As described in detail above, the plurality of pores 104 proximal to second surface region 108 allow for ingrowth of bone in the plurality of pores 104, thereby aiding the initial fixation of orthopaedic implant 200 to the bone B.

FIG. 9b also illustrates bone cement 120 which is applied to and received within the plurality of pores 104 of first surface region 106 of orthopaedic implant 200 as described above. The bone cement 120 applied to the top of first surface region 106 may then be further shaped (prior to or during implantation of orthopaedic implant 200) to fill the remainder of void V and reconstructing the contour of canal of bone B.

Additionally, according to an embodiment of the instant disclosure at least a portion of femoral stem 304 may itself be formed of open porous metal as disclosed herein. Thus, when femoral stem 304 is implanted into the femoral canal C, bone cement 120 applied to first surface region 106 of orthopaedic implant 200 may also be at least partially received within the open porous metal comprising femoral stein 304, thereby aiding in initial fixation of femoral stein 304.

Figure 10B:
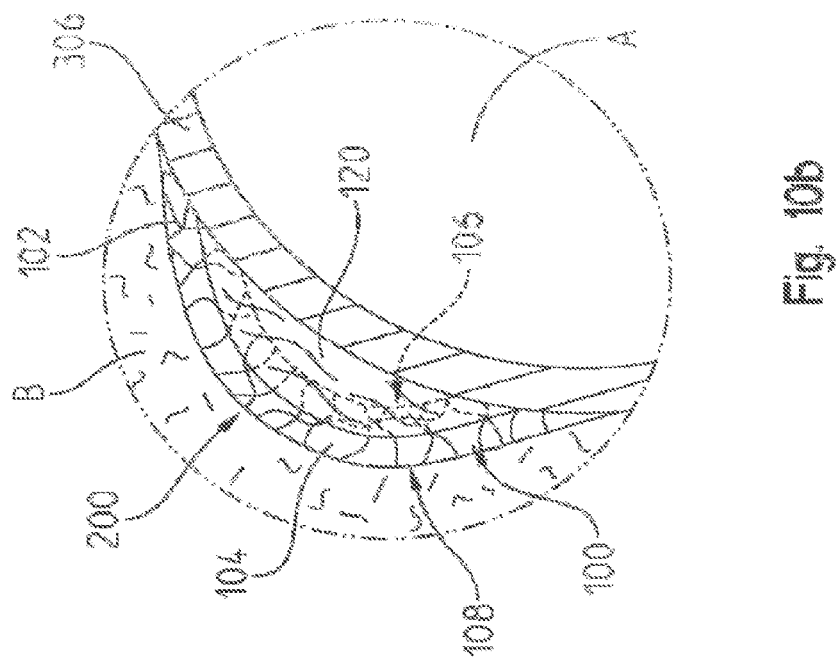
FIG. 10*b* is an enlarged view of the orthopaedic implant implanted within the void of FIG. 10*a*.
Figure 10A:
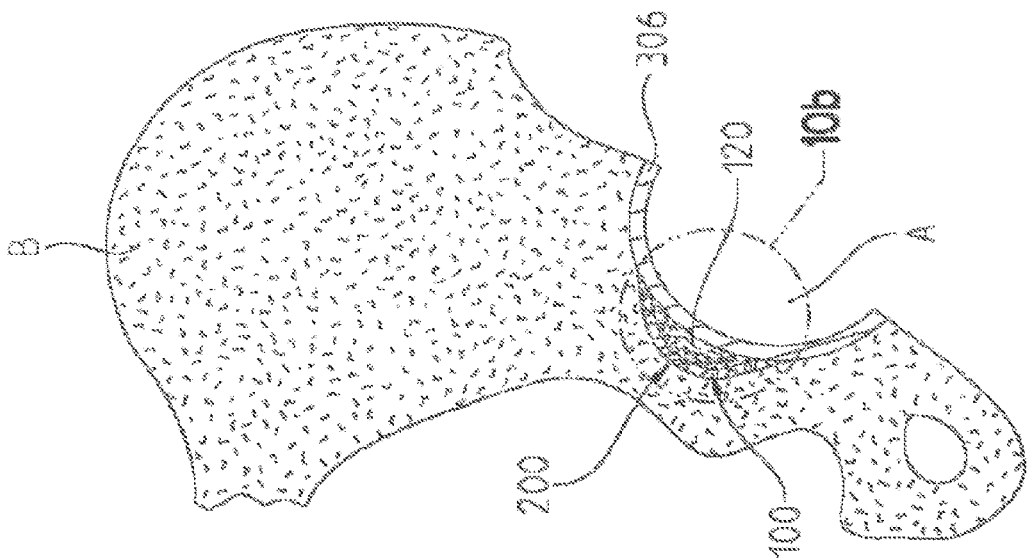
FIG. 10*a* is a cross-sectional view illustrating an orthopaedic implant according to the present disclosure implanted within a void in the acetabulum.

Referring to FIGS. 10a and 10b, yet another illustration of an embodiment of orthopaedic implant 200 being used to fill a void V in a bone B (shown here as the acetabulum) is depicted. As shown, orthopaedic implant 200 is used to fill a void V in a bone B prior to affixation of acetabular cup 306 to the acetabulum.

With reference to FIG. 10b, orthopaedic implant 200 is orientated in the void V such that second surface region 108 contacts the bone B outing the void V. As described in detail above second surface region 108 allows for ingrowth of bone into the plurality of pores 104 proximal second surface region 108, thereby aiding the initial fixation of orthopaedic implant 200 to the bone B.

Further, orthopaedic implant 200 may be utilized during an orthopaedic implant revision procedure. With reference to FIGS. 10a and 10b, orthopaedic implant 200 may be utilized during a hip implant revision procedure for filling void V within the acetabulum. As depicted in FIG. 10a, use of orthopaedic implant 200 for filling void V in the acetabulum during a revision procedure, allows a surgeon to implant a revision acetabular cup 306 (of identical size to the prior acetabular cup) without requiring removal of additional bone stock from the surface of the acetabulum.

As with FIGS. 8b and 9b, FIG. 10b also illustrates bone cement 120 which is applied to and received within the plurality of pores 104 of first surface region 106 of orthopaedic implant 200. The bone cement 120 applied to the top of first surface region 106 may then be further shaped (prior to or during implantation of orthopaedic implant 200) to fill the remainder of void V and reconstruct the contour of the missing acetabular bone B.

Additionally, according to an embodiment of the instant disclosure at least a portion of the outer hemispherical surface of acetabular cup 306 may itself be formed of open porous metal as disclosed herein. Thus, when acetabular cup 306 is implanted within the acetabulum, bone cement 120 applied to the first surface region 106 of orthopaedic implant 200 may be at least partially received within the open porous metal comprising acetabular cup 306, thereby aiding in the initial fixation of acetabular cup 306.

Figure 11:
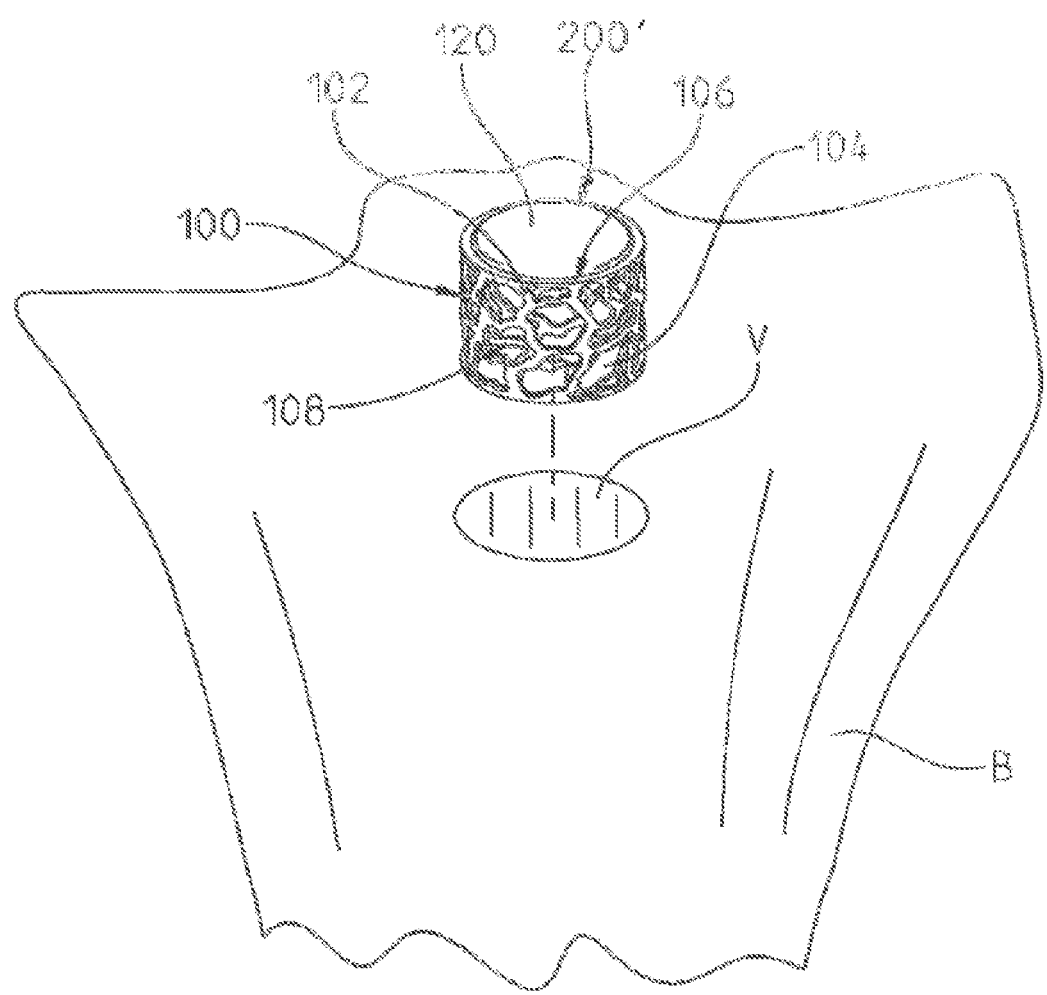
FIG. 11 is a perspective view showing implantation of the orthopaedic implant of FIG. 5*a* into a void in a tibia.

With reference to FIG. 11, an illustrative embodiment of orthopaedic implant 200 (similar to orthopaedic implant 200 disclosed in FIG. 5a) being used to fill a void V in a bone B (shown here as a proximal tibia) is depicted. By way of example, void V may have resulted following removal of a portion of the proximal tibia during procurement of a portion of the patellar tendon for use as a graft.

As shown, orthopaedic implant 200' is oriented in the void V such that second surface region 108 contacts the bone B lining the void V. As described above, second surface region 108 allows for ingrowth of bone into the plurality of pores 104 proximal second surface region 108, thereby aiding the initial fixation of orthopaedic implant 200' to the bone B.

As with other embodiments of orthopaedic implant 200 described herein, bone cement 120 aides in shaping orthopaedic implant 200' such that second surface region 108 contacts the bone B lining the void V. Bone cement 120 further aides in replacing and reconstructing the contour of the missing bone B.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method for filling a bone void, comprising:
   obtaining a pliable sheet-like orthopedic implant product that can be reshaped during a surgical implantation procedure for filling a bone void, wherein the pliable sheet-like orthopedic implant product includes an open porous metal sheet having a first side opposite a second side with a curable fixative disposed along the first side of the open porous metal sheet, the curable fixative received in pores along the first side of the open porous metal sheet and extending to a depth within the open porous metal sheet, the curable fixative absent from pores along the second side of the open porous metal sheet; and
   implanting the pliable sheet-like orthopedic implant product in the bone void such that the second side of the open porous metal sheet contacts bone, wherein said implanting includes reshaping the pliable sheet-like orthopedic implant product from a first shape to a second shape the second side of the open porous metal sheet is contacting bone.

2. The method of claim 1, wherein said pores along the first side of the open porous metal sheet have a first nominal pore size, and wherein said pores along the second side of the open porous metal sheet have a second nominal pore size that is less than the first nominal pore size.

3. The method of claim 1, wherein said curable fixative includes an externalized portion that remains external of said open porous metal sheet to provide an exposed outermost surface of the pliable sheet-like orthopedic implant product, said curable fixative further including an internal zed portion that is continuous with said externalized portion, said internalized portion extending to said depth within said open porous metal sheet.

4. The method of claim 3, wherein said curable fixative, despite providing said exposed outermost surface of the pliable sheet-like orthopedic implant product, extends into said open porous metal sheet to approximately halfway between the first side and the second side of said open porous metal sheet.

5. The method of claim 1, wherein said curable fixative covers the first side of the open porous metal sheet.

6. The method of claim 1, wherein said curable fixative provides an external layer of curable fixative atop the first side of the open porous metal sheet.

7. The method of claim 1, wherein said open porous metal sheet comprises a porous substrate coated with a biocompatible metal that infiltrates and coats surfaces of the porous substrate.

8. The method of claim 1, wherein said reshaping the pliable sheetlike orthopedic implant product from the first shape to the second shape molds the pliable sheetlike orthopedic implant product to the shape of the bone void.

9. The method of claim 1, wherein said reshaping the pliable sheetlike orthopedic implant product from the first shape to the second shape reshapes the curable fixative.

10. The method of claim 1 in combination with implanting an additional orthopedic implant adjacent the bone void such that the curable fixative is positioned between an outer surface of the additional orthopedic implant and the second side of the open porous metal sheet.

11. The method of claim 1, wherein the pliable sheetlike orthopedic implant product also is reshaped immediately prior to the second side of the open porous metal sheet contacting bone.

12. An orthopedic surgical method, comprising:
obtaining a pliable sheet-like orthopedic implant product that can be reshaped during a surgical implantation procedure for filling a bone void, wherein the pliable sheet-like orthopedic implant product includes an open porous metal sheet having a first side opposite a second side with a curable fixative disposed along the first side of the open porous metal sheet to provide an exposed outermost surface of the pliable sheet-like orthopedic implant product, said curable fixative including an externalized portion that remains external of said open porous metal sheet to provide said exposed outermost surface of the pliable sheet-like orthopedic implant product, said curable fixative further including an internalized portion that is continuous with said externalized portion, said internalized portion extending to a depth within said open porous metal sheet through a first group of pores along the first side of the open porous metal sheet, wherein the open porous metal sheet includes a second group of pores along the second side of the open porous metal sheet that are unoccupied by the curable fixative;
implanting the pliable sheet-like orthopedic implant product in the bone void such that the second side of the open porous metal sheet contacts bone, wherein said implanting includes reshaping the pliable sheet-like orthopedic implant product from a first shape to a second shape while the second side of the open porous metal sheet is contacting bone; and
implanting an additional orthopedic implant adjacent the bone void such that the externalized portion of the curable fixative is positioned between an outer surface of the additional orthopedic implant and the second side of the open porous metal sheet.

* * * * *

UNITED STATES PATENT AND TRADEMARK OFFICE
CERTIFICATE OF CORRECTION

PATENT NO. : 9,539,095 B2  
APPLICATION NO. : 14/513345  
DATED : January 10, 2017  
INVENTOR(S) : Monaghan et al.

It is certified that error appears in the above-identified patent and that said Letters Patent is hereby corrected as shown below:

In the Claims

In Column 12, Line 57, in Claim 1, after "shape", insert --while--

In Column 13, Line 1, in Claim 3, delete "internal zed" and insert --internalized--, therefor Signed and Sealed this  
Twelfth Day of June, 2018

Andrei Iancu  
*Director of the United States Patent and Trademark Office*